United States Patent [19]
Takano et al.

[11] Patent Number: 5,314,418
[45] Date of Patent: May 24, 1994

[54] CANNULA

[75] Inventors: Hisateru Takano; Yoshiyuki Taenaka; Takeshi Nakatani; Eisaku Sasaki, all of Suita; Susumu Kashiwabara; Takashi Kimura, both of Otsu, all of Japan

[73] Assignee: Toyo Boseki Kabushiki Kaisha, Japan

[21] Appl. No.: 118,281

[22] Filed: Sep. 9, 1993

Related U.S. Application Data

[63] Continuation of Ser. No. 762,343, Sep. 19, 1991, abandoned.

[30] Foreign Application Priority Data

Sep. 21, 1990 [JP] Japan ................. 2-253938

[51] Int. Cl.$^5$ .......................................... A61M 25/00
[52] U.S. Cl. .................................. 604/282; 604/280
[58] Field of Search ............................ 604/280-282, 604/164, 264, 170, 95; 128/656-658, 772

[56] References Cited

U.S. PATENT DOCUMENTS

| | | | |
|---|---|---|---|
| 3,885,561 | 5/1975 | Cami | 604/280 |
| 4,117,836 | 10/1978 | Erikson | 604/281 |
| 4,140,119 | 2/1979 | Pollack | 604/280 |
| 4,173,981 | 11/1979 | Mortensen | 604/282 |
| 4,747,840 | 5/1988 | Ladika et al. | 604/281 |
| 4,784,639 | 11/1988 | Patel | 604/53 |
| 4,804,359 | 2/1989 | Grunwald et al. | 604/284 |
| 4,838,879 | 6/1989 | Tanabe et al. | 604/280 |
| 4,882,777 | 11/1989 | Narula | 604/281 |
| 4,886,506 | 12/1989 | Lovgren et al. | 604/280 |
| 4,935,017 | 6/1990 | Sylvanowicz | 604/281 |
| 4,960,410 | 10/1990 | Pinchuk | 604/280 |
| 5,041,084 | 8/1991 | De Vries et al. | 604/43 |

Primary Examiner—John D. Yasko
Assistant Examiner—Manuel Mendez
Attorney, Agent, or Firm—Wegner, Cantor, Mueller & Player

[57] ABSTRACT

There is disclosed a draining cannula to be connected with the left atrium which comprises a tip portion (A), a curvature portion (B) connected with said tip portion and a body tubular portion (C) connected with said curvature portion. The length and the outer diameter of said cannula is sufficient for inserting the cannula into the femoral vein and for reaching the tip portion the left atrium passing through the cava, the right atrium and the interatrial septum. The portion (B) is made of a material which is more flexible than that of said portion (C). A resilient spiral thin wire is provided within the thickenss of the wall part defining the lumen of the curvature portion (B). The cannula is used for draining from the left atrium by inserting it into the femoral vein and passing the tip portion (A) of said cannula through the cava, the right atrium and the interatrial septum to reach the left atrium, without thoracotomy.

4 Claims, 5 Drawing Sheets

CANNULA

This application is a continuation of U.S. application Ser. No. 07/762,343 filed Sep. 19, 1991, and now abandoned.

FIELD OF THE INVENTION

The present invention relates to an artificial organ which maintains systemic circulation of a patient suffering from depression of heart function to improve heart function. More particularly, it relates to a draining cannula for introducing arterial blood oxygenated by the lung into a pump placed outside the body.

BACKGROUND OF THE INVENTION

With the progress of medicine, new treatments have positively been attempted to apply to various cases, wherein to save patients by conventional treatments is difficult, and many good results have been obtained. Among them, regarding treatments for heart diseases such as cardiac infarction, valvular disease of the heart and the like, the saving rate of patients has significantly been improved by development of pharmacotherapy as well as technical improvement in cardiotomy due to the progress of pump-oxygenators and cardiomuscular protection. Further, for patients suffering from depression of heart function, circulation assisting devices such as intra-aortic balloon pumping (hereinafter abbreviated as "IABP"), veno-arterial bypass (hereinafter abbreviated as "VAB") and the like have been developed and it is possible to assist heart function for several days to several weeks. IABP is used for assisting heart function by inserting an elongated balloon into the aorta from the femoral artery and inflating and deflating the balloon in the aorta. VAB is used for draining (or drainaging) venous blood from a patient, oxygenating the blood by an artificial lung and returning the oxygenated blood to the patient by a pump. However, even IABP and VAB are yet insufficient for assisting heart function and, therefore, some patients cannot be saved by IABP and VAB. For such patients, a systemic heart assisting artificial heart having larger efficiency for assisting heart function is used in the clinical field. Such a systemic heart assisting artificial heart is used by inserting a draining cannula in the left atrium during thoracotomy, connecting a blood prefusion cannula to the aorta and connecting both cannulas to the inlet and outlet of a blood pump placed outside the body, respectively and driving the pump to assist heart function. For the systemic heart assisting artificial heart, the shape and insertion site of the cannula upon draining from the left atrium are of importance. Because of its nature, the device is requested to assist heart function for several days. During this period of time, the chest is closed and only the cannulas penetrate the wall of the chest to protrude outside the body. Therefore, when the cannulas oppress the heart or other organs, sufficient dehematization cannot be obtained. Further, the oppressed organs are adversely affected and, therefore, shape fitness for the living body is more important in comparison with that of cannulas used in ordinary cardiotomy.

For this purpose, the cannula should have an enough diameter for obtaining shape fitness for the living body as well as sufficient draining and, therefore, a special shape is required. In view of this, one cannula for the assisting artificial heart is proposed in Japanese Patent Kokai No. 58-177664.

One key problem which is usually encountered with in the use of the assisting artificial heart is that to fit and remove the device require much time and labor. The assisting artificial heart is fitted by inserting a draining cannula and a blood perfusion cannula under extracoporeal circulation with a pump-oxygenator after exposing the heart by thoracotomy. Therefore, it is difficult to use it for a patient requiring urgent treatment. Further, when the assisting artificial heart is removed after heart function is recovered, repair must be made after withdrawal of the cannulas by thoracotomy. This problem is not yet solved even by using the above cannula disclosed in Japanese Patent Kokai No. 58-177664.

OBJECTS OF THE INVENTION

The main object of the present invention is to provide a draining cannula for a systemic heart assisting artificial heart which is readily fitted and removed and, further, is safely used.

This object as well as other objects and advantages of the present invention will become apparent to those skilled in the art from the following description with reference to the accompanying drawings.

SUMMARY OF THE INVENTION

According to the present invention, there is provided a cannula which comprises a tip portion (A), a curvature portion (B) connected with said tip portion and a body tubular portion (C) connected with said curvature portion;

the length and the outer diameter of said cannula being, at least, 300 mm and, at most, 12 mm, respectively;

the length of said portion (A) and said portion (B) being 10 to 50 mm and 20 to 100 mm, respectively;

said portion (B) being made of a material which is more flexible than that of said portion (C);

a resilient spiral thin wire provided within the thickness of the wall part defining the lumen of said curvature portion (B) and extending over, at least, 20 mm in length of said portion (B); and said cannula being used for draining from the left atrium by inserting it into the femoral vein and passing the tip portion (A) of said cannula through the cava, the right atrium and the interatrial septum to reach the left atrium, without thoracotomy.

The present invention also provides a method for assisting blood circulation by using the cannula of the present invention. Further the present invention provides a method for draining from the left atrium without thoracotomy.

DETAILED DESCRIPTION OF THE INVENTION

Figure 1:
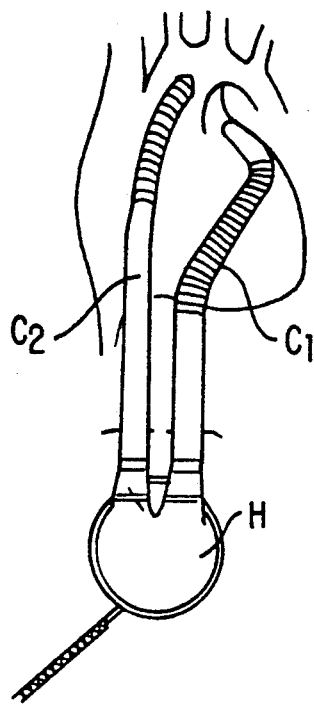
FIG. 1 is a schematic diagram illustrating fitting of a conventional systemic heart assisting artificial heart by thoracotomy.

As seen from FIG. 1, for fitting a conventional systemic heart assisting artificial heart (H) to a patient, a draining cannula (C₁) of a conventional systemic heart assisting artificial heart (H) is inserted to the left atrium by thoracotomy. A blood feeding cannula (C₂) is inserted to the aorta.

The cannula of the present invention can be fitted to and removed from a patient suffering from depression of heart function without thoracotomy.

As the material of the cannula, for example, there can be used polyvinyl chloride containing a plasticizer (e.g., diethylhexylphathalate, etc.), polydimethylsiloxsane, polyurethane and the like. Further, it is preferred that the surface of the lumen of the cannula which contacts with blood is coated with an antithrombogenic material which hardly causes blood coagulation. The antithrombogenic material is not specifically limited and there can be used a known material such as polyurethane, preferably, segmented polyether type urethane or segmented polyether type urethane urea, polyurethane-polydimethylsiloxane block or graft copolymer, polyvinyl chloride containing a high molecular weight plasticizer (e.g., polyester, polyurethane, etc.), a material wherein a physiological active substance such as heparin, urokinase, prostaglandin or the like is immobilized on its surface, a material exhibiting antithrombogenic properties by slowly releasing heparin which is bound to the surface thereof through ionic-bond, or the like.

The cannula of the present invention has a tip portion (A), a curvature portion (B) connected with the tip portion and a body tubular portion (C) connected with the curvature portion. The length of the cannula is, at least, 300 mm, normally, 400 to 700 mm. The external diameter of the cannula is, at most, 12 mm φ, normally, 5 to 10 mm φ. The length of the portion (A) is 10 to 50 mm, normally, 15 to 30 mm and the length of the portion (B) is 20 to 100 mm, normally, 30 to 90 mm.

The portion (B) is made of a material which is more flexible than that of the portion (C) to prevent the cannula from bending upon insertion of the cannula and from collapsing due to negative pressure upon draining. Preferably, the portion (B) has a Shore hardness of, at most, 70D, preferably, 45A to 65D, and the portion (C) has a Shore hardness of, at least, 80A, preferably, 90A to 75D.

The resilient spiral thin wire is wound about and provided within the thickness of the wall part defining the lumen of the curvature portion (B) and extending over, at least, 20 mm, normally, 40 to 80 mm in length of the portion (B). The spiral thin wire prevents the cannula from kinking. The spiral pitch of the wire is preferably 0.8 to 10 mm, preferably, 1.5 to 5 mm.

The cannula of the present invention is used for draining from the left atrium by inserting it from the femoral vein and passing the tip portion (A) of said cannula through the cava, the right atrium and the interatrial septum to reach the left atrium, without thoracotomy. The drained blood can be circulated through a pump and a blood perfusion cannula connected with, for example, the femoral artery to form an assisting blood circulation without thoracotomy.

As described hereinabove, the cannula of the present invention is fitted to and removed from a patient without thoracotomy and, therefore, by using the cannula of the present invention, cardiotomy which is required in the conventional treatment is not required. Thereby, it becomes possible to reduce infection and a burden given to various organs by cardiotomy as well as to remarkably reduce expenses relating to operation and the patient's mental burden.

PREFERRED EMBODIMENT OF THE INVENTION

Figure 2:
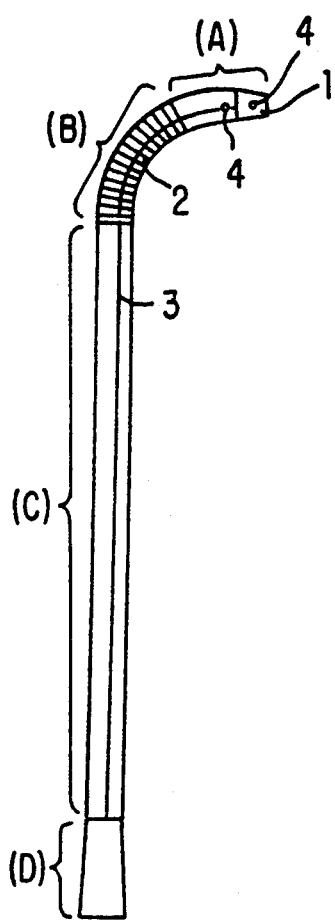
FIG. 2 is a schematic diagram illustrating one embodiment of the cannula of the present invention.
Figure 3A:
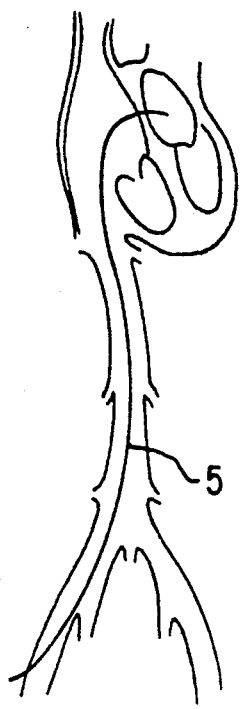
FIGS. 3a to 3f are schematic diagrams illustrating the steps for fitting the cannula of the present invention.
Figure 3B:
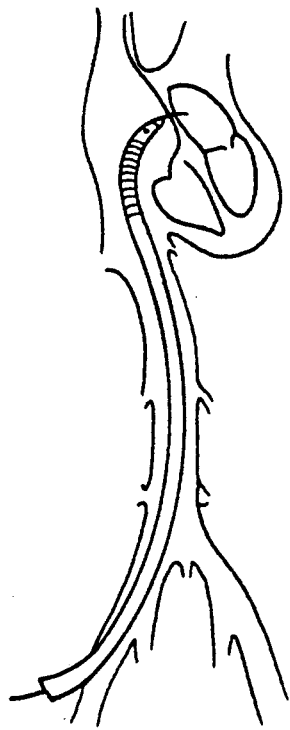
Figure 3C:
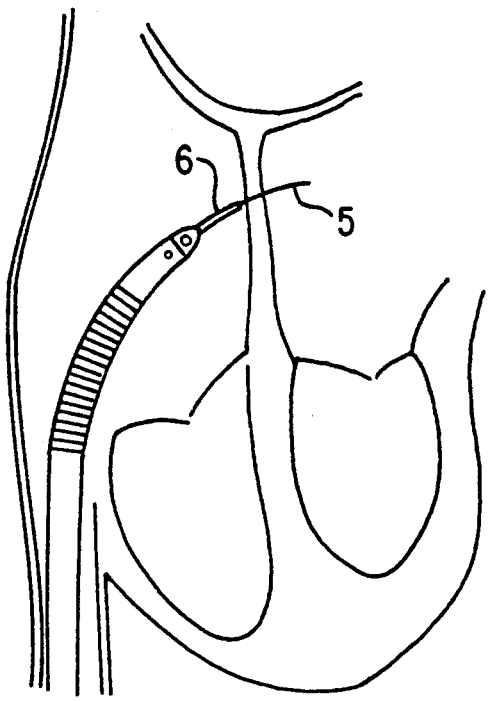
Figure 3D:
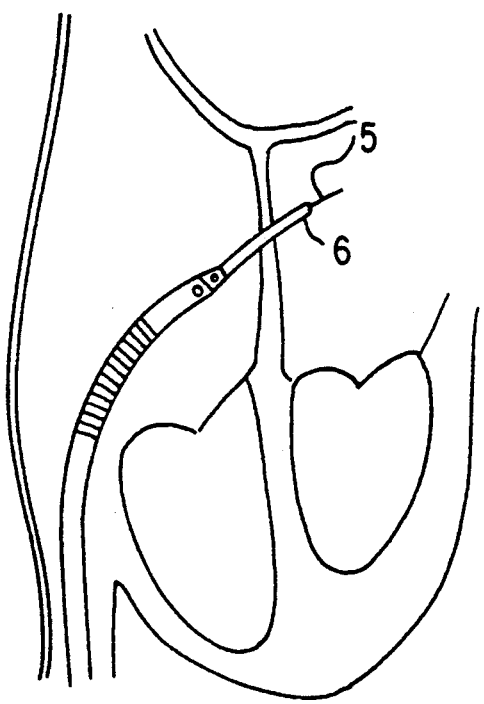
Figure 3E:
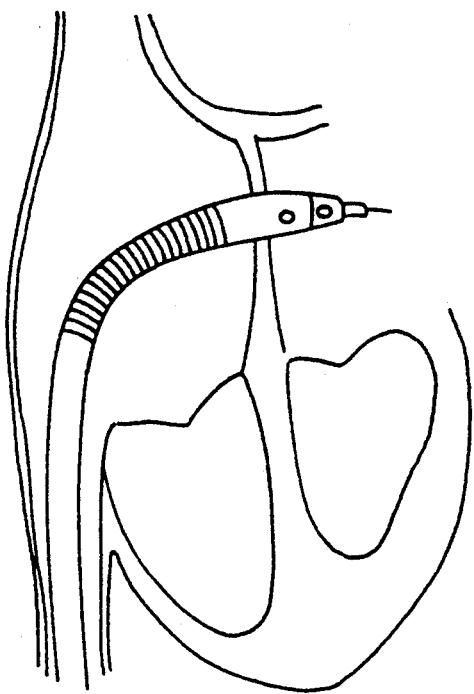
Figure 3F:
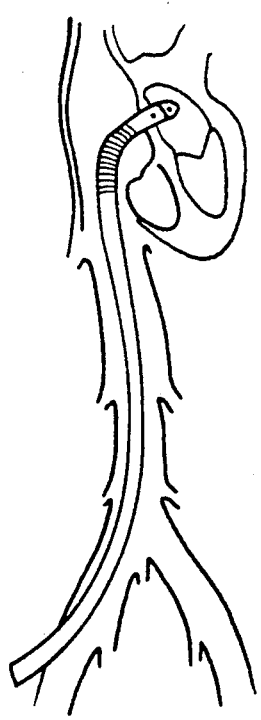
Figure 4:
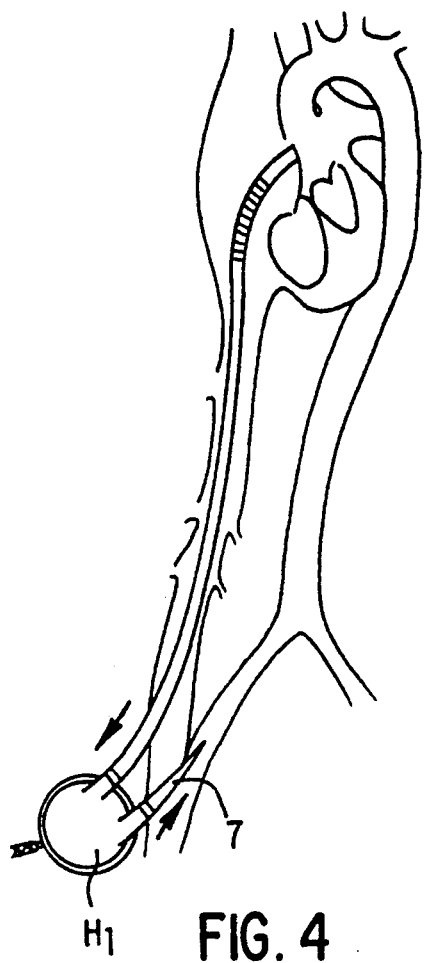
FIG. 4 is a schematic diagram illustrating the assisted circulation using the cannula of the present invention.

Now, referring to FIGS. 2 to 4, a preferred embodiment of the present invention is illustrated in detail.

FIG. 2 shows a schematic side view of a preferred embodiment of the cannula of the present invention. As shown in FIG. 2, the cannula is curved at about 70° with respect to the central axis of the body tubular portion (C) at the position about 30 mm from the distal end. The structure of the cannula can be divided roughly into four portions (A) to (D). The portion (A) is the tip portion which is inserted into the left atrium through the interatrial septum and, particularly, the portion can be provided with a tapered tip 1 at the end thereof so as to facilitate the insertion. Further, in order to facilitate dehematization, holes 4 can be provided not only on the tip but also on a side part other than the tip. Preferably, the portion (A) includes a radio-opaque portion 3 which can form the image by irradiation of X-ray so that the retention of this part in the left atrium can be confirmed by X-ray. The portion (B) is a curvature portion which flexes to reach the portion (A) the left atrium. The portion (B) should have two properties which are inconsistent with each other, i.e., flexibility for easy bending and strength for preventing kinking of the cannula upon bending. Therefore, the portion (B) is composed of a material which is more flexible than that of the other portions and, further, a resilient thin wire 2 is embedded in the wall of the material in a spiral form so as to prevent kinking upon bending. It is preferred that the hardness of the portion (B) is 45A to 65D (Shore hardness). When the spiral pitch of the wire is too small, flexibility of this portion is lost and, when the spiral pitch is too large, kinking is scarcely prevented. Therefore, the spiral pitch of the wire is 0.8 to 10 mm, preferably, 1.5 to 5 mm. By this treatment, it becomes possible to satisfy the above inconsistent requirements. The material of the wire is not limited to a specific one and the wire can be made of, for example, steel, stainless steel, carbon, an organic high resilient material (e.g., Kebler ®, Normex ®, etc.) or the like. Regarding the portion (C), in order to prevent the cannula from bending when it is inserted and to prevent the cannula from collapsing when negative pressure is applied upon draining, a larger hardness than that of the portion (B) is requested. Preferably, the hardness of the portion (C) is 90A to 75D (Shore hardness) In this embodiment, the raido-opaque line 3 is provided through the portions (A) to (C) so as to confirm the position thereof in the body. Regarding the portions (A) to (C), the outer diameter is not more than 12 mm so as to pass through the vein of the human body and, further, a smaller wall thickness is preferred so as to obtain a sufficient flow under a limited diameter. However, when the wall thickness is too small, the cannula is liable to be collapsed by negative pressure applied upon draining. Therefore, the wall thickness is 0.3 to 2.0 mm, preferably 0.5 to 1.5 mm. The portion (D) is a connector for connecting with an external circuit or pump. This portion can be connected with the cannula in advance or attached after insertion of the cannula in the body.

The fitting procedure of the cannula of the present invention is shown in FIGS. 3a to 3f. Firstly, a guide wire 5 is inserted from the femoral part and it is retained in the left atrium by using a commercially available Brockenbrough needle (FIG. 3a). Then, a cannula is inserted along the guide wire 5 until the tip of the cannula reach the right atrium (FIG. 3b). A director 6 for expanding a hole of the interatrial septum is inserted into the cannula along the guide wire until it reaches the front of the interatrial septum (FIG. 3c). Then, the hole of the interatrial septum is expanded by the director 6 (FIG. 3d). The cannula is inserted into the left atrium along the director (FIG. 3e). The guide wire 5 and director 6 are withdrawn. Thus, fitting of the cannula of the present invention is completed (FIG. 3f). This procedure is one embodiment of the insertion method and is not specifically limited thereto. One embodiment of assisted circulation using the cannula of the present invention is shown in FIG. 4. Arterial blood dehematized by the cannula of the present invention is supplied into the body by a blood feeding cannula 7 which is connected with the femoral artery through a pump. FIG. 4 shows an air-driving type assisting artificial heart (H) which is generally used as an assisting artificial heart and, further, the pump may be a centrifugal pump or roller pump.

Further, it is possible to remove the artificial heart after heart function is recovered by merely pulling the cannula of the present invention at the externally extruded part. The hole in the interatrial septum opened by the cannula will be spontaneously closed and cured after withdrawal.

The cannula of the present invention can be smoothly inserted into the left atrium without thoracotomy. The dehematized blood can be fed through a pump to the body. Therefore, an assisted circulation can be performed without thoracotomy.

What is claimed is:

1. A cannula which comprises a tip portion (A), a curvature portion (B) connected with said tip portion and a body tubular portion (C) connected with said curvature portion, said cannula having a lumen longitudinally extending through the tip portion, the curvature portion and the body tubular portion;
    the length and the outer diameter of said cannula being, at least, 300 mm and, at most, 12 mm, respectively;
    the length of said tip portion (A) and said curvature portion (B) being 10 to 50 mm and 20 to 100 mm, respectively;
    said curvature portion (B) being made of a material which is more flexible than that of said body tubular portion (C);
    a resilient spiral thin wire provided within the thickness of the wall part defining the lumen of said curvature portion (B) and extending over, at least, 20 mm in length of said curvature portion (B);
    wherein said cannula is adapted to be inserted into the femoral vein with the tip portion (A) passing through the cava, the right atrium and the interatrial septum to reach the left atrium, for draining from the left atrium without thoracotomy; and
    wherein the material of the curvature portion (B) has a Shore hardness of 45A to 65D and the body tubular portion (C) has a Shore hardness of 90A to 75D.

2. A cannula according to claim 1, wherein the length of the cannula is 400 to 700 mm and the outer diameter of the cannula is 5 to 10 mm.

3. A method for assisting blood circulation which comprises draining a blood from the left atrium by a cannula a cannula having a tip portion (A), a curvature portion (B) connected with said tip curvature portion, said cannula having a lumen longitudinally extending through the tip portion, the curvature portion and the body tubular portion;
    the length and the outer diameter of said cannula being, at least, 300 mm and, at most, 12 mm, respectively;
    the length of said tip portion (A) and said curvature portion (B) being 10 to 50 mm and 20 to 100 mm, respectively;
    said curvature portion (B) being made of a material which is more flexible than that of said body tubular portion (C);
    a resilient spiral thin wire provided within the thickness of the wall part defining the lumen of said curvature portion (B) and extending over, at least, 20 mm in length of said curvature portion (B);
    inserting said cannula into the femoral vein with the tip portion (A) of said cannula passing through the cava, the right atrium and the interatrial septum to reach the left atrium for draining there from, without thoracotomy; and
    draining blood being perfused to the femoral artery by a femoral arterial cannula.

4. A method for draining from the left atrium which comprises inserting a cannula having a tip portion (A), a curvature portion (B) connected with said tip portion and a body tubular portion (C) connected with said curvature portion into the femoral vein, and passing the tip portion (A) of said cannula through the cava, the right atrium and the interatrial septum to reach the left atrium, without thoracotomy, said cannula having a lumen longitudinally extending through the tip portion, the curvature portion and the body tubular portion;
    the length and the outer diameter of said cannula being, at least, 300 mm and, at most, 12 mm, respectively;
    the length of said tip portion (A) and said curvature portion (B) being 10 to 50 mm and 20 to 1090 mm, respectively;
    said curvature portion (B) being made of a material which is more flexible than that of said body tubular portion (C); and
    a resilient spiral thin wire provided within the thickness of the wall part defining the lumen of said curvature portion (B) and extending over, at least, 20 mm in length of said curvature portion (B).

* * * * *